United States Patent [19]

Blum

[11] 4,368,389
[45] Jan. 11, 1983

[54] PHOTON EMISSION TOMOGRAPHIC APPARATUS AND METHOD

[76] Inventor: Alvin S. Blum, 2350 Del Mar Pl., Fort Lauderdale, Fla. 33301

[21] Appl. No.: 163,057

[22] Filed: Jun. 26, 1980

[51] Int. Cl.³ .............................................. G01T 1/20
[52] U.S. Cl. .................................. 250/363 S; 378/20
[58] Field of Search ............ 250/361 R, 363 S, 445 T, 250/446, 447, 439 R; 369/324, 325

[56] References Cited

U.S. PATENT DOCUMENTS

| 4,150,294 | 4/1979 | Hounsfield | 250/445 T |
| 4,216,381 | 8/1980 | Lange | 250/363 S |
| 4,220,861 | 9/1980 | Colombo et al. | 250/363 S |
| 4,223,222 | 9/1980 | Gray et al. | 250/363 S |
| 4,278,888 | 7/1981 | Wagner | 250/445 T |

FOREIGN PATENT DOCUMENTS 2040138 8/1980 United Kingdom ............ 250/445 T

Primary Examiner—Davis L. Willis

[57] ABSTRACT

Tomographic imaging system employs large area, collimated scintillation detector rotated around radiation emitting subject. Detector support rotates with an inner ring inside a stationary outer ring. Counterbalanced detector support arm is forced by spring action to cause collimator face to follow body contour as detector rotates around the body, thereby reducing collimator to subject distance to improve system resolution. Includes adjustable subject support system.

11 Claims, 8 Drawing Figures

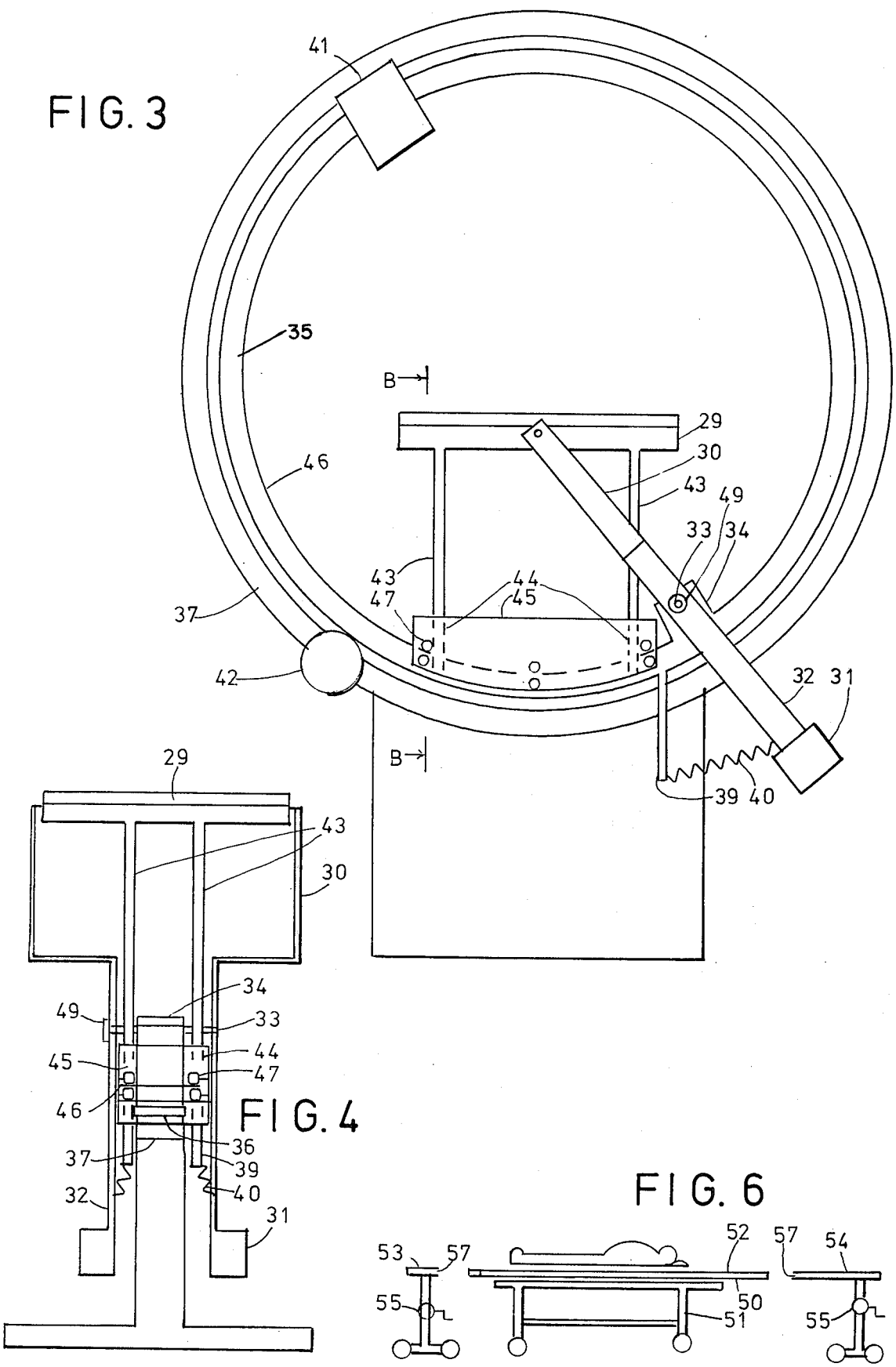

PHOTON EMISSION TOMOGRAPHIC APPARATUS AND METHOD

BACKGROUND OF THE INVENTION

1. Field of the Invention

Apparatus and method for producing images of the distribution in three dimensions of photon emitting materials (radioactive pharmaceuticals) in the body including detector, detector support and body support.

2. Description of the Prior Art

Area radiation detectors of the scintillation camera type rotate around the subject containing radioactive material so as to view the radiation from a plurality of angles. Radiation detection information and detector position information are correlated by computer reconstruction to provide images of the distribution of the radioactive material within the body in a variety of views such as transverse or longitudinal slices through the body. Prior art uses one or more scintillation detectors in a rotating ring. The radius of the cylinder described by the moving face of the detector is generally fixed large enough to accommodate a large person. Resolution or image quality of these detection systems deteriorates rapidly as the subject/detector distance increases so that a fixed radius unnecessarily sacrifices image quality in a smaller subject. General Electric Corp. has recently introduced a rotating counterbalanced detector (see enclosed brochure) whose radius of rotation can be adjusted before operation to a smaller cylinder to view the head or a child with shorter subject/detector distance.

However, the shape of the body and the illustrated cantilevered body support are not cylindrical, so that imaging the torso requires setting the radius to allow the detector to clear the support sides which means that when the detector is over the chest, it may be very far from the body surface, causing a loss of image resolution. Further, the geometry of the counterweight support requires a cantilevered body support. The cantilevered body support requires great strength and rigidity of construction, interfering with design for adjustability to smaller bodies and thin construction for transparency to the radiation which must pass therethrough to the detector. The counterbalance mechanism is effective mechanical engineering because the counterweight for the detector head provides rotational balance as well, so that only small uniform force for rotation is required at any angle. Unfortunately, the biological engineering is not as effective, because the rotating counterweight and ring geometry interfere with extending the arms overhead. Arms at the side increase the radius of the cylinder of rotation needlessly and also absorb imaging radiation from the torso.

SUMMARY OF THE PRESENT INVENTION

It is an object of the present invention to improve image quality by minimizing subject/detector distance. The present invention allows the radius of rotation to change during rotation to conform to the body contour, maintaining minimum subject/detector distance throughout the procedure. Improved body support means allows adjustment to body size and reduces absorbing structure. Improved detector support design allows improved patient positioning, because body may now be supported and extended at both ends without interference from counterweight.

The present invention provides one or more collimated, large area radiation imaging detector devices generally of, but not limited to, the scintillation camera type, including means for supporting said detector, means for moving said detector about a radiation emitting subject so as to view the subject from a plurality of angles. Means are provided to maintain close spacing between subject and detector during said movement to achieve optimum resolution of imaging of distribution of radiation emitting material within the subject. It is an object of the present invention to provide detector means of a generally rectangular shape to further facilitate close spacing without interference from body parts of the subject. The round or hexagonal shape of current detectors prohibit close spacing to certain anatomic regions. Body contour belt means may be provided to cover and approximate the body contours and to provide a sliding contact path for the detector. It is a further object of the invention to provide spring loaded detector support means to gently and yieldably press the detector against the body contours, body support means, body contour belt means and the like during its movement or rotation about the body. The body and detector act generally as cam and cam follower in this operation. Surfaces of a lubricous nature and guides on the leading edge of the detector may be provided to facilitate smooth movement therebetween. Counterweight means are provided at the opposite end of the detector support means to balance the mass of the detector so that as it moves in space, the only force of the face of the detector against the body, belt, or the like is a controlled spring force. Support counterweight means may be further provided to balance the weight of the entire detector with its support means and counterweight means, thereby allowing the movement of the detector about the subject with relatively small and uniform force by support driving means. Improved body support means are provided allowing adjustment to body size and shape. Said body support means facilitate patient handling and positioning, reduce radiation absorbtion and enable closer patient/detector spacing.

BRIEF DESCRIPTION OF THE DRAWINGS

FIG. 3 is a front view of an embodiment wherein the detector as it adjusts to body contours, swings in a plane perpendicular to the axis of rotation around the body.

FIG. 4 is a partial cross section through line B—B of FIG. 3.

FIG. 6 is a side view of the flexible web support means.

DESCRIPTION OF THE PREFERRED EMBODIMENTS

Figure 1:
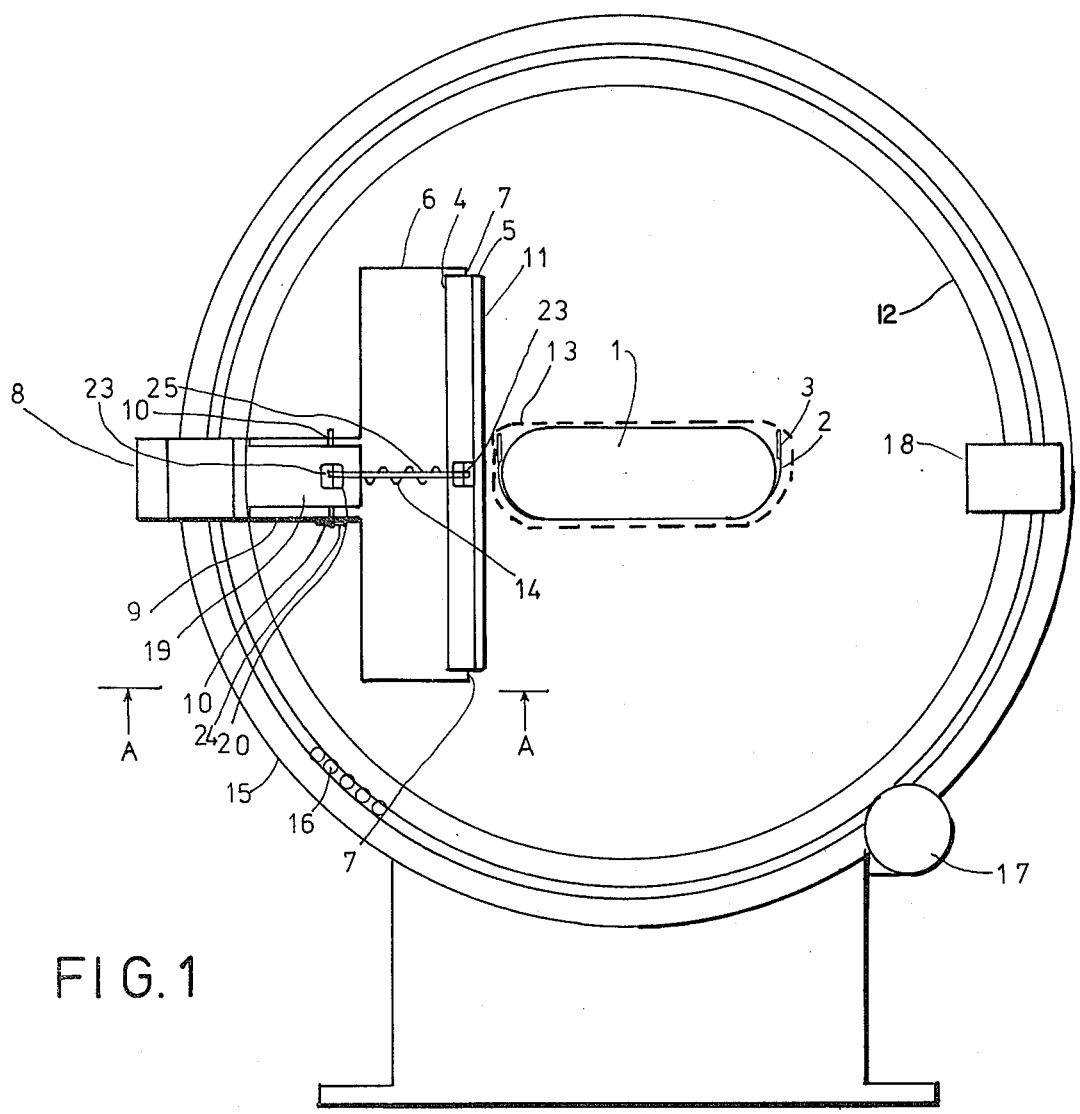
FIG. 1 is a front view of an embodiment of the invention wherein the detector, as it adjusts to body contours, swings in a plane parallel to the axis of rotation around the body.
Figure 2:
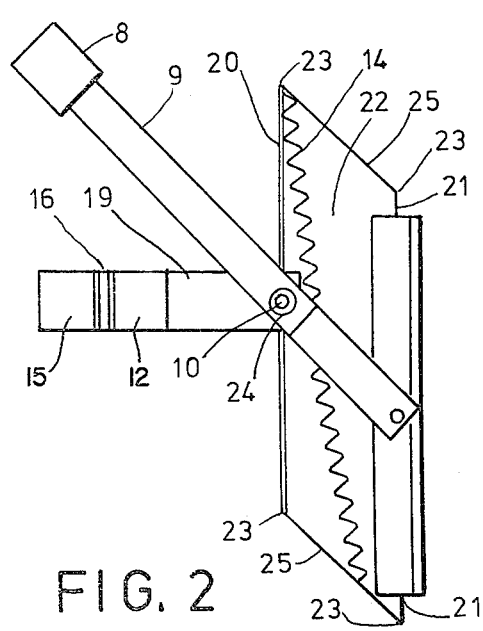
FIG. 2 is a partial cross section through line A—A of FIG. 1.

FIGS. 1 and 2 show in front view and partial section through line A—A of FIG. 1 respectively, a tomographic system of the present invention. Radiation from the patient 1, supported in fabric sling 2, suspended from rigid longitudinal members 3, is detected by scintillation camera detector 4, having parallel hole collimator 5. Detector 4 is held in yoke 6 at pivot points 7. Detector counterweight 8 balances weight of the detector in any position so that only a small force is required to swing detector support arm 9 about pivots 10 to move collimator face 11 into or out of inner ring 12 to maintain contact with flexible body contour belt 13 wrapped around the patient at the level of the detector. Tension spring 14 provides this small, controlled force, gently following the patient contours as inner ring 12 rotates inside stationary outer ring 15 on roller bearings 16, driven by small motor 17. Assembly counterweight 18 balances entire weight of detector, detector counterweight, and detector support assembly so that only a small driving force is required. A second detector and support may replace this counterweight. Use of small spring force and small drive motor reduce potential hazard to patient. Detector support arm pivots 10 are fastened to inner ring projection 19, whose center line is always on a radius of rotation of inner ring 12. Also fastened to projection 19 are parallelogram arms 20. Parallelogram bars 25 connect arm 20 to projections 21 at opposite ends of the detector by pivots 22 to form a parallelogram with a diagonal spring 14. In any position of the detector as it swings in and out while following the body contour as inner ring 12 rotates, parallelogram action will maintain the collimator face 11 in a plane parallel to the axis of rotation of ring 12. This geometry facilitates tomographic reconstruction. Drive motor 17 may rotate the inner ring in uniform increments, e.g. 36 steps of 10° each; pausing at each step to accummulate radiation data from angles all around the body. Alternatively the ring may turn and data may be input continuously. Computer processing and display means, not illustrated, accumulate and process the input radiation and position data and provide useful images of the distribution of radiation emitting material in the body. As the detector rotates to measure the patient from all angles, it is desirable that there be no longitudinal motion of the patient relative to the detector i.e. motion along the axis of rotation of ring 12. Unfortunately, as detector 4 swings in support arm 9 around pivots 10, this longitudinal motion does occur. Fortunately, the amount of longitudinal motion can be calculated if the angle of arm 9 with projection 19 is known. Rotary position indicator 24 provides this information to the computer, which calculates the longitudinal position and displaces the incoming data by this distance, thereby correcting for the motion. A small portion of the caudad and rostrad edges of the field of view will thereby have incomplete data and may not be as useful. Alternatively, the patient or detector assembly may be moved by mechanical means the corresponding distance. FIG. 3 is a front view and FIG. 4 is a partial section through B—B of FIG. 3 of another tomographic system embodying the invention. A collimated detector 29, held in yoke 30 is counterbalanced by 2 detector counterweights 31 at the end of detector support arms 32 pivoted at pivots 33 in inner ring projection 34 carried by inner ring 35 which rotates on roller bearings 36 inside stationary outer ring 37. Inner ring also carries spring supports 39. Tension springs 40 between supports 39 and arms 32 force detector face toward center of ring and against the body of the patient, not shown. As ring 35 rotates around the body, the detector gently, by action of springs 40, follows the contour of the body, body support, body contour covering belt wrapped around the body, or the like. Detector assembly counterweight 41, fastened to ring 35 balances the mass of the detector assembly so that very low force drive motor 42 can rotate ring 35 around the patient.

The detector support arm of the embodiment in FIG. 1 moves in a plane parallel to the axis of the ring, whereas the detector support arm of FIG. 3 moves in a plane perpendicular to the axis of the ring. Different correcting means to maintain geometry suitable for tomography are therefor required. In the embodiment of FIG. 3 in order to keep the same point on the face of detector 29 perpendicular to a radius of ring 35 as arms 32 swing through an arc, rods 43 are rigidly fastened at right angles to the back of detector 29. Rods 43 slide in sleeves 44 in light weight flange rider 45, which rides on flange 46 on inner edge of inner ring 35 on rollers 47. Uniform angular incremental rotation of ring 35 will not result in uniform angular rotation of detector 29 if the angle of arm 32 with spring support 39 changes. Rotary position indicator 49 detects the angle and feeds that information into the computer. The computer can then operate drive motor 42 to achieve the appropriate rotational angle of the detector.

Figure 7:
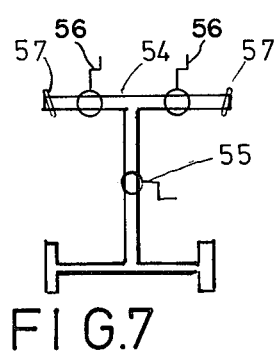
FIG. 7 is an end view of one adjustable end support for flexible web body support means.
Figure 5:
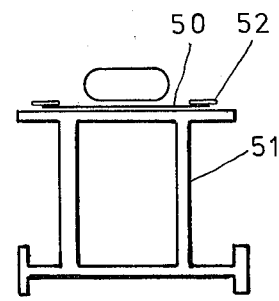
FIG. 5 is an end view of the flexible web body support means in use for patient transfer.

FIGS. 5, 6, 7 illustrate a body support system for rotational tomography employing a flexible web such as a stiff fabric sling or hammock 50. It is shown resting on a conventional patient transport stretcher 51 in FIGS. 5 and 6. Rigid, longitudinal, radiolucent, support members 52 may be permanently fastened to edges of sling 50, or may slide into edge pockets after patient is moved onto sling to reduce discomfort. The stretcher 51 is rolled into place with overhanging members 52 projecting into the ring. Long adjustable end support 54 is rolled into place from the opposite face of the ring and adjusted for height with adjustor 55 and for width with adjustor 56 until longitudinal members 52 fit into sockets 57. Short adjustable end support 53 is now fitted to the other ends of the members 52. Width and height of the sling are adjusted to remove the stretcher 51 and to center the region of the body for optimum tomography.

Figure 8:
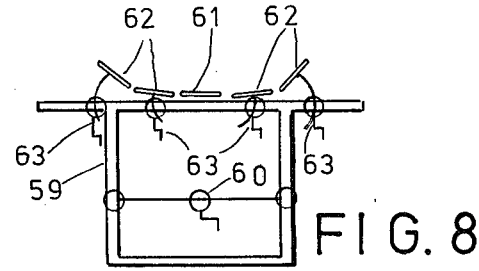
FIG. 8 is an end view of rigid plank body support means.

FIG. 8 illustrates a body support system which remains in place straddling the rotating ring with an end support 59 at each end, having height adjustor 60. The body is supported therebetween by rigid radiolucent planks 62 and 61. All four side planks 62 are adjustable by adjustors 63 and also removable. With all the planks in place and flat, the patient is positioned by sliding. The planks are removed or adjusted as required by body size and contour. To facilitate detector head movement and reduce patient trauma, a body contour belt may be wrapped around the body at the level to be traversed by the detector. Body contour belt may be a wide band of thin metal, heavy plastic or fabric having thick edges to raise the belt off the body slightly. The edges are far enough apart to be beyond the caudad and rostrad edges of the field of view of the detector.

Inasmuch as the present invention is subject to many variations, modifications and changes in detail, it is intended that all matter described above or shown in the accompanying drawings be interpreted as illustrative and not in a limiting sense.

What is claimed is:

1. A rotational tomographic imaging system for detecting and displaying the distribution in depth of radiation emitting materials within a body with collimated radiation detector means and body support means, comprising: detector support means; detector rotation means; and body contour following means, said body contour following means causing the collimator face to be adjacent to the surface of said body and said body support means as said detector means is rotated about said body to minimize detector/body distance for improved image resolution.

2. The invention of claim 1, further comprising body support means including: flexible body support web means; rigid longitudinal member means for supporting said web means along its edges; and adjustable end support means for supporting the ends of said longitudinal member means, wherein said adjustable end support means provide for a first, generally flat configuration of said body support means to facilitate transfer of said body and a second configuration generally conforming to the contours of said body to minimize detector/body distance during detector rotation.

3. The invention of claim 1, further comprising body support means including rigid longitudinal plank means for supporting said body; adjustable end plank support means for supporting and adjusting said planks, wherein said adjustable end plank support means provide for a first, generally flat configuration of said body support means to facilitate transfer of said body and a second configuration generally conforming to the contours of said body to minimize detector/body distance during detector rotation.

4. The invention of claim 1, wherein a parallelogram assembly maintains the face of said collimator in a plane parallel to the axis of said rotation.

5. The invention of claim 4, wherein diagonal spring means provide the force causing said detector means to follow said body contour.

6. The invention of claim 1, wherein said detector rotation means includes rotating carrier means carrying said detector support means, said detector support means having arm means counterbalanced by counterweight means.

7. The invention of claim 6 wherein paired pivoted arm means extend on opposite sides of said ring means wherein each arm means carries counterweight means.

8. The invention of claim 6, wherein said arm moves in a plane parallel to the axis of rotation of said carrier means, including means to maintain the face of said detector means perpendicular to a radius of rotation during said contour following.

9. The invention of claim 6, wherein said arm means moves in a plane perpendicular to the axis of rotation of said carrier means, including means to maintain the face of said detector means perpendicular to a radius of rotation during said body contour following.

10. The invention of claim 1, including position indicating means to communicate body contour following motions to computer means for appropriate correction for computer image reconstruction.

11. A structure for a scintillation camera having detector means for emission tomography analysis of a patient, comprising: detector support means; rotation means for rotating said detector and support means about an axis and around said patient so as to view said patient from a plurality of angles; radius adjusting means to adjust the radius of rotation of said detector during said rotation to maintain a minimum distance between said detector and said patient; said detector support means including means to maintain the face of said detector tangential to the arc of rotation and parallel to the axis of rotation.

* * * * *